(12) United States Patent
Davison et al.

(10) Patent No.: US 7,056,322 B2
(45) Date of Patent: Jun. 6, 2006

(54) BONE FASTENER TARGETING AND COMPRESSION/DISTRACTION DEVICE FOR AN INTRAMEDULLARY NAIL AND METHOD OF USE

(75) Inventors: Dale George Davison, Warsaw, IN (US); Paul S. Cooper, Washington, DC (US)

(73) Assignee: Depuy Orthopaedics, Inc., Warsaw, IN (US)

( * ) Notice: Subject to any disclaimer, the term of this patent is extended or adjusted under 35 U.S.C. 154(b) by 318 days.

(21) Appl. No.: 10/108,679

(22) Filed: Mar. 28, 2002

(65) Prior Publication Data

US 2004/0215204 A1    Oct. 28, 2004

(51) Int. Cl.
*A61B 17/58* (2006.01)
*A61F 2/00* (2006.01)

(52) U.S. Cl. ........................................ 606/98
(58) Field of Classification Search ............... 606/53, 606/60, 62, 64, 86, 87, 98, 102, 105, 96, 606/97, 90, 104, 54, 67, 57, 58, 59
See application file for complete search history.

(56) References Cited

U.S. PATENT DOCUMENTS

| | | | |
|---|---|---|---|
| 4,456,004 A * | 6/1984 | Kenny | 606/57 |
| 4,541,424 A | 9/1985 | Grosse et al. | |
| 4,667,664 A | 5/1987 | Taylor et al. | |
| 4,848,368 A * | 7/1989 | Kronner | 606/57 |
| 4,976,713 A | 12/1990 | Landanger et al. | |
| 5,234,434 A | 8/1993 | Goble et al. | |
| 5,304,177 A * | 4/1994 | Pennig | 606/58 |
| 5,314,426 A * | 5/1994 | Pohl et al. | 606/58 |
| 5,350,380 A * | 9/1994 | Goble et al. | 606/80 |
| 5,352,228 A | 10/1994 | Kummer et al. | |
| 5,354,300 A * | 10/1994 | Goble et al. | 606/80 |
| 5,433,720 A * | 7/1995 | Faccioli et al. | 606/87 |
| 5,474,561 A | 12/1995 | Yao | |
| 5,620,449 A | 4/1997 | Faccioli et al. | |
| 5,776,194 A | 7/1998 | Mikol et al. | |
| 6,039,739 A | 3/2000 | Simon | |
| 6,039,742 A * | 3/2000 | Krettek et al. | 606/96 |
| 6,514,253 B1 * | 2/2003 | Yao | 606/53 |
| 6,663,656 B1 * | 12/2003 | Schmieding et al. | 606/232 |
| 2002/0151897 A1 * | 10/2002 | Zirkle, Jr. | 606/62 |

* cited by examiner

*Primary Examiner*—Eduardo C. Robert
*Assistant Examiner*—Anu Ramana
(74) *Attorney, Agent, or Firm*—Maginot, Moore & Beck

(57) ABSTRACT

An intramedullary nail fastener targeting and bone compression/distraction device provides bone fastener alignment and compression or distraction of the bone. The intramedullary nail fastener targeting and bone compression/distraction device has a nail carrier portion, a bone fastener alignment and drill jig portion, and a compression/distraction mechanism. Various sizes of intramedullary nails are retained by the device while alignment carriages provides for proper drilling of the bone and placement of bone fasteners such as screws. The compression/distraction mechanism provides measured compression or distraction of the bone prior to final bone fastener placement.

34 Claims, 12 Drawing Sheets

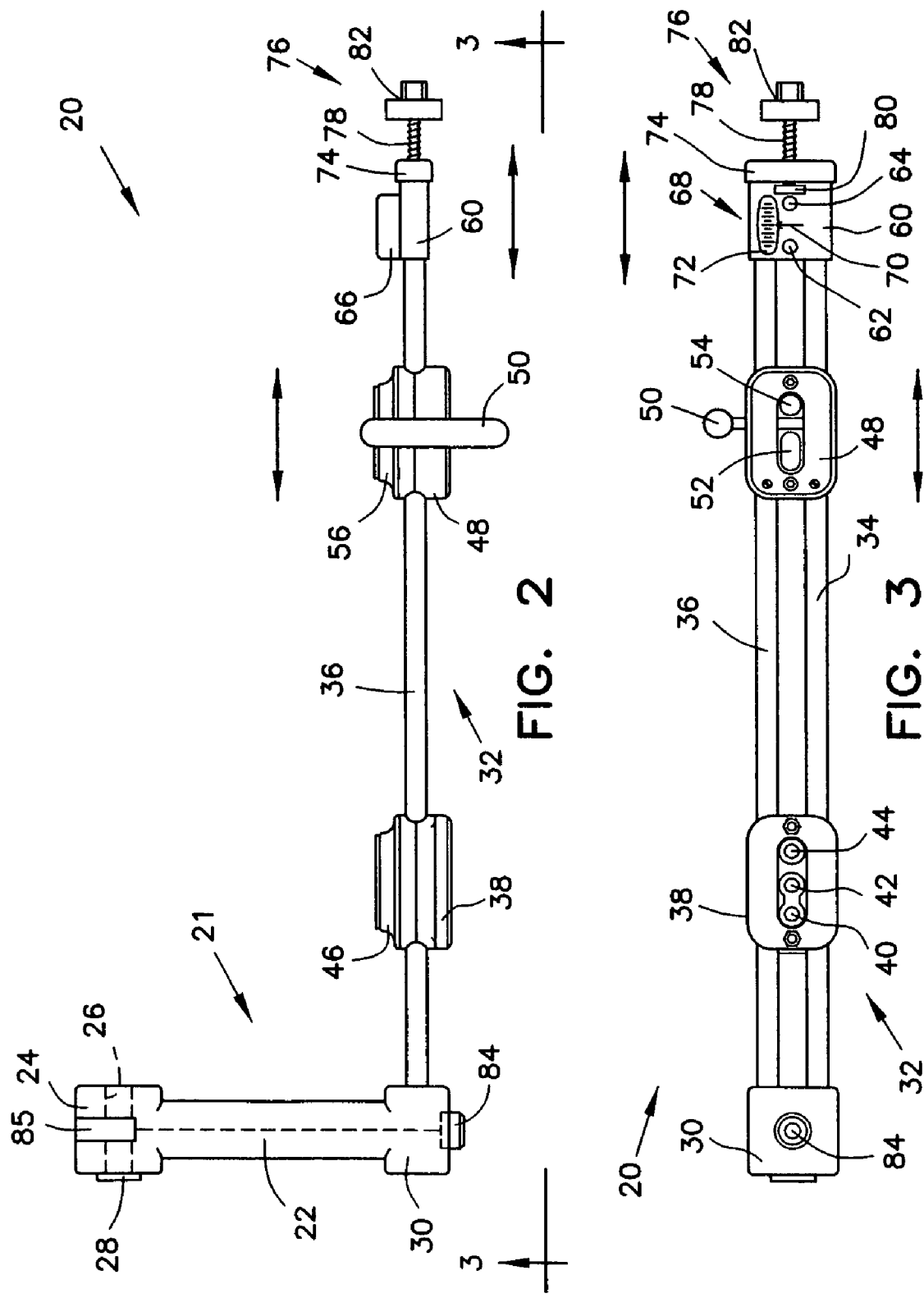

BONE FASTENER TARGETING AND COMPRESSION/DISTRACTION DEVICE FOR AN INTRAMEDULLARY NAIL AND METHOD OF USE

TECHNICAL FIELD OF THE INVENTION

The present invention relates to implantation and fixation of intramedullary nails and, more particularly, to a bone fastener targeting and compression/distraction device and method of use for implantation and fixation of an intramedullary nail.

BACKGROUND OF THE INVENTION

Intramedullary nails of the type used herein have two spaced holes or bores that extend diametrically across the intramedullary nail near the distal end thereof and with two spaced holes or bores of a similar nature near the proximal end thereof. These holes or bores are formed in the nail to accept or allow bone screws or fasteners to extend therethrough in order to fix the intramedullary nail to a bone or various bone fragments for the healing process. Since the bone screws are installed after the intramedullary nail has been inserted into the patient, such bone screw holes or bores are said to be "blind" in terms of bone-drilling alignment that must be achieved. Since the intramedullary nail is implanted into the patient, a problem exists with assuring correct alignment for drilling through the bone in order that a screw placed through the drilled hole also goes through a correct hole of the intramedullary nail.

Because of this problem, many devices have been devised that aid in assuring correct alignment of bone screws and the intramedullary nail. It has been recognized by inventors of these devices that one method of determining where the intramedullary nail is located within the bone is to manufacture the device from radiolucent materials that allow radiographs to be made. In connection with this problem, other devices have been designed to pivot out of the way to allow radiographs to be made. Additionally, surgeons often also use external fixation devices to maintain alignment and length.

In addition to assuring correct alignment for the implantation of an intramedullary nail in order to effect repair of a bone, it is also desirable to provide compression and/or distraction with respect to the mending of the bone. Typically, such compression is applied independently of the intramedullary nail alignment problem. One known intramedullary nail targeting guide, however, also provides compression. This device provides compression by applying pressure against soft tissue. Compression of soft tissue, however, typically causes soft tissue damage. Such soft tissue damage is generally not acceptable.

In view of the above, what is thus needed is an improved system of targeting bone fasteners for alignment with holes in the intramedullary nail.

What is further needed is a bone fastener targeting device that provides bone compression.

What is still further needed is a bone fastener targeting device that provides bone distraction.

SUMMARY OF THE INVENTION

In one form, the subject invention is a bone fastener targeting and compression device and procedure of use for intramedullary nails. In another form, the subject invention is a bone fastener targeting and distraction device and procedure of use for intramedullary nails.

In one form, the subject invention provides a targeting device for an intramedullary nail. The targeting device includes an intramedullary nail holder, and arm, a support, first and second bone fastener targeting blocks, and a bone fixator. The arm extends from the intramedullary nail holder. The support extends from the arm. The first bone fastener targeting block is fixedly mounted on the support. The second bone fastener targeting block is movably mounted on the support. The bone fixator is mounted on the support and configured to provide compression to a bone.

In another form, the subject invention provides an intramedullary nail bone fastener targeting apparatus that includes an intramedullary nail holder, an arm extending from the intramedullary nail holder, and a support extending from the arm. The intramedullary nail bone fastener targeting apparatus further includes a fixed bone fastener targeting block positioned on the support to align with a first set of holes in any one of various lengths of intramedullary nails, a movable bone fastener targeting block positioned on the support to align with a second set of holes in any one of the various lengths of intramedullary nails, and a bone fixation mechanism positioned on the support and operative to provide compression or distraction to a bone in which the intramedullary nail is inserted.

In yet another form, the subject invention provides an intramedullary nail bone fastener targeting device that includes an arm, a support, a first bone fastener targeting block, a second bone fastener targeting block, and a bone fixation block. The arm has a first end and a second end with the first end configured to receive an intramedullary nail holder that is configured to receive an intramedullary nail. The support extends from the second end. The first bone fastener targeting block is fixedly retained on the support and includes a plurality of bores therethrough that are alignable with first bores in one end of an intramedullary nail that is adapted to be received by the intramedullary nail holder. The second bone fastener targeting block is movably retained on the support and includes a plurality of bores therethrough that are alignable with second bores in another end of the intramedullary nail that are distal from the first bores regardless of length of the intramedullary nail. The bone fixation block is movably retained on the support and includes a bore therethrough that is adapted to retain a fixator that is attached to a bone, wherein the bone fixation block provides compression or distraction of the bone via movement along the support while retain the fixator.

BRIEF DESCRIPTION OF THE DRAWINGS

FIG. 2 is a side view of the exemplary bone fastener targeting and compression/distraction guide for an intramedullary nail of FIG. 1;

FIG. 3 is a bottom view of the exemplary bone fastener targeting and compression/distraction guide for an intramedullary nail of FIG. 1 taken along line 3—3 of FIG. 2;

Corresponding reference characters indicate corresponding parts throughout the several views. Like reference characters tend to indicate like parts throughout the several views.

DETAILED DESCRIPTION OF THE INVENTION

Figure 1:
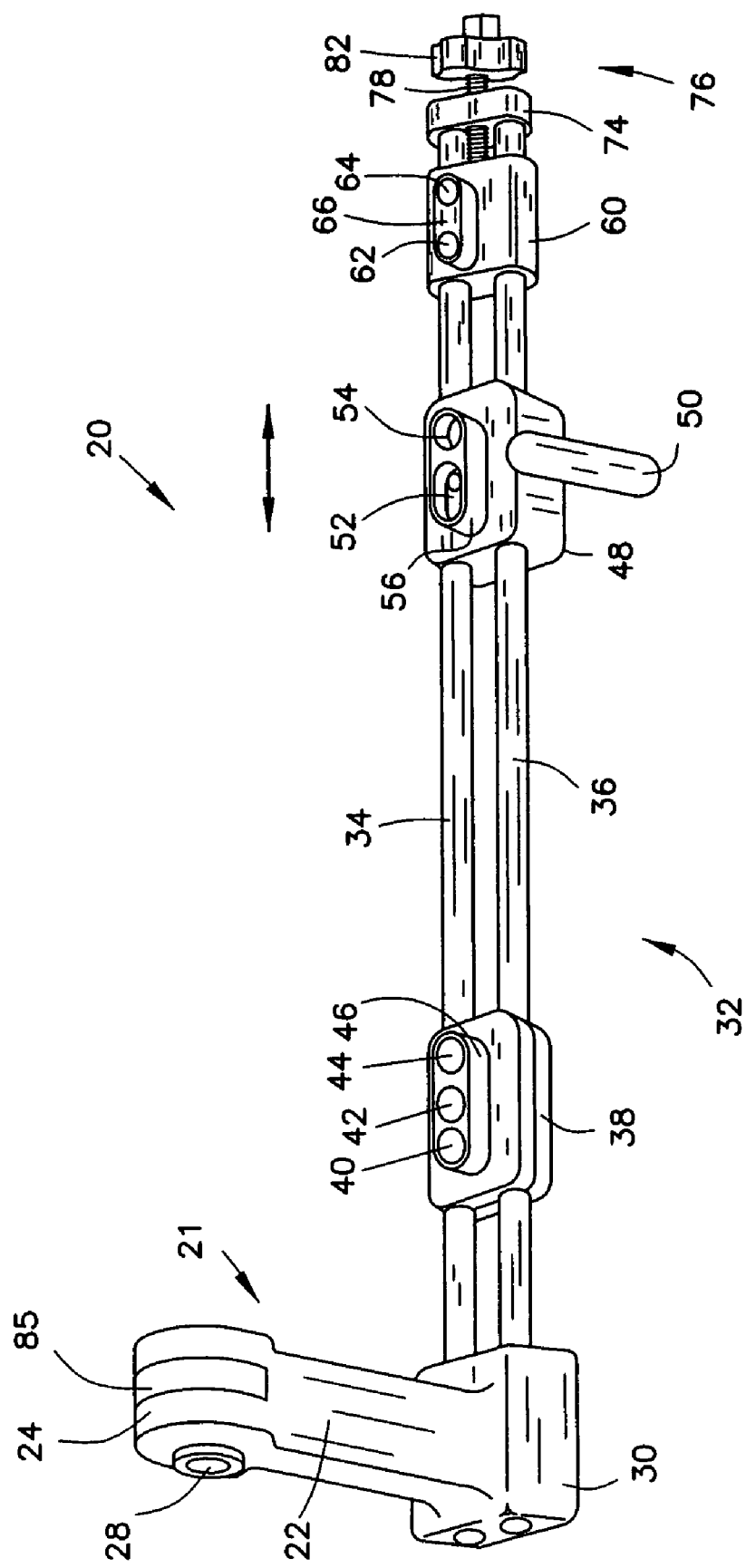
FIG. 1 is a perspective view of an exemplary bone fastener targeting and compression/distraction guide, jig or device for an intramedullary nail in accordance with the principles of the subject invention.

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring now to FIGS. 1–3 there is shown an exemplary embodiment of a guide, jig or device for inserting an intramedullary nail, targeting bone fasteners with respect to the inserted intramedullary nail, and provide bone compression and/or distraction (or external fixation device) for an intramedullary nail generally designated 20 (hereinafter referred to as "intramedullary nail fastener targeting and bone compression/distraction device" for simplicity only and not for limitation thereof). The intramedullary nail fastener targeting and bone compression/distraction device 20 is configured, adapted and/or operative to allow insertion or placement of an intramedullary nail into an intramedullary canal of a bone, bones and/or bone fragments (collectively hereinafter "bone"), provide alignment for bone fasteners such as screws with the inserted intramedullary nail, provide a jig or guide for securing the bone fasteners through the bone and the intramedullary nail as appropriate, and provide compression and/or distraction of the bone.

To this end, the intramedullary nail fastener targeting and bone compression/distraction device 20 has a nail carrier portion 21, a bone fastener alignment and drill jig portion 32, and a compressor-distractor/compression-distraction adjustor/adjustment mechanism 76. The nail carrier portion 21 is configured, adapted, and/or operative to releasably retain an intramedullary nail prior to, during, and after insertion of the intramedullary nail into a medullary canal of a bone and allow the alignment portion 32 and the compression-distraction adjustor 76 to rotate, swing or pivot about the inserted intramedullary nail as appropriate. Additionally, the nail carrier portion 21 is configured, adapted and/or operative to orient an intramedullary nail for bone fastener alignment.

The bone fastener alignment and drill jig portion 32 is configured, adapted and/or operative to allow/provide alignment of bone fasteners, screws and/or the like with the particular size (i.e. length) of inserted intramedullary nail and orientation thereof (i.e. a medial-lateral, M-L, orientation or an anterior-posterior, A-P, orientation). Additionally, the bone fastener alignment and drill jig portion 32 is also configured, adapted and/or operative to function as a jig, guide or external fixation device for preparation (e.g. drilling) of the bone for receiving the bone fasteners.

The compression-distraction adjustor 76 is configured, adapted and/or operative to provide compression and/or distraction of the bone. The compression/distraction adjustor 76 also provides an indication of compression and/or distraction. Particularly, there is provided a means to show measured compression and/or distraction such as actual force applied in a compression mode and/or in a distraction mode.

Figure 8:
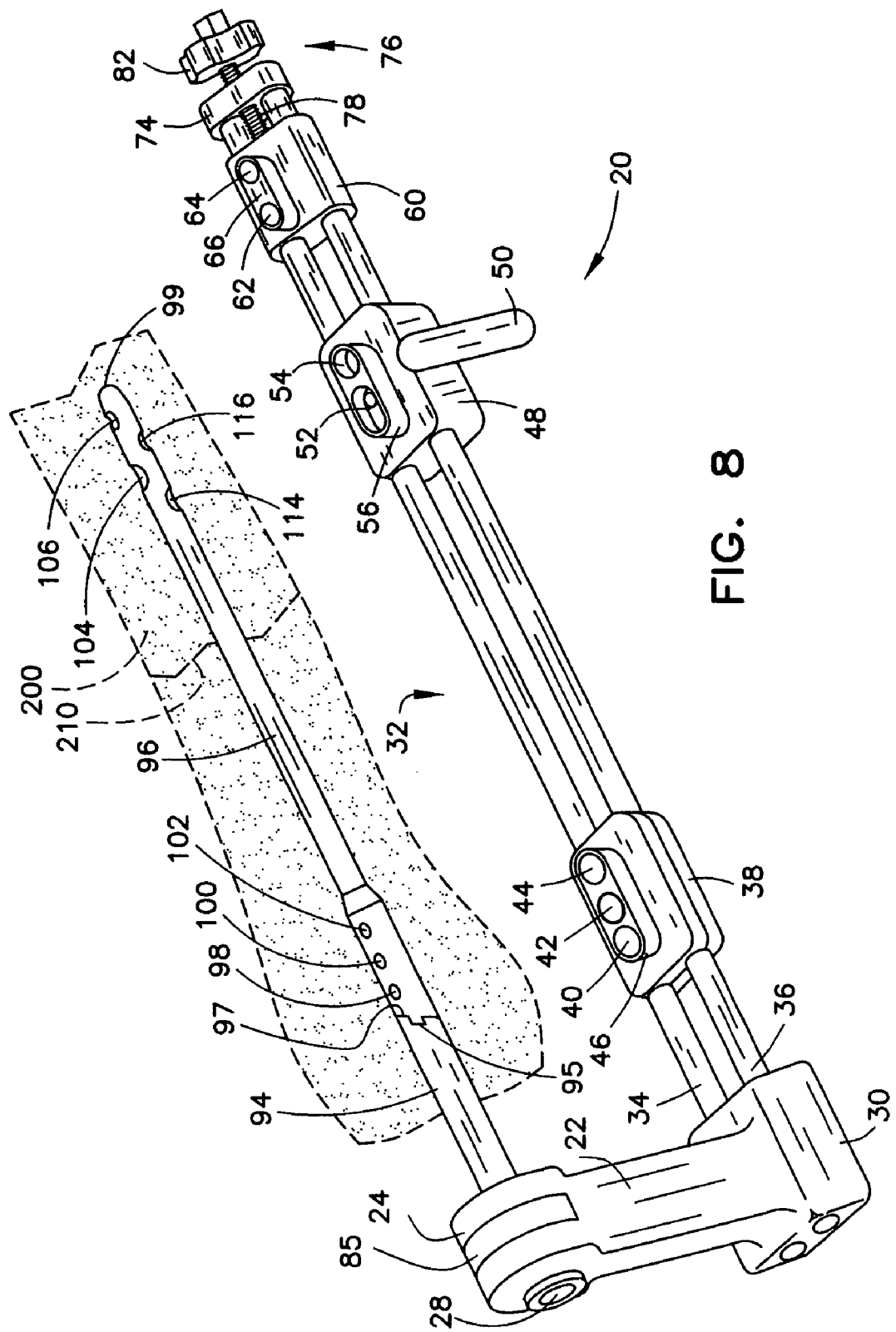
FIG. 8 is a perspective view of the exemplary bone fastener targeting and compression/distraction guide for an intramedullary nail of FIG. 1 shown retaining an intramedullary nail.

Particularly, the nail carrier 21 includes a nail arm 22 having a first end 24 and a second end 30. It should be appreciated that the nomenclature "first" and "second" is arbitrary and therefore may be interchanged without consequence. The first end 24 is configured, adapted and/or operative to retain an intramedullary nail and thus may be alternatively referred to as a nail retention carrier 24. While not necessarily the case, the nail retention carrier 24 is embodied as a generally round structure. The nail retention carrier 24 includes a bore 26 that extends axially therethrough. As seen in FIG. 8, the bore 26 is configured, adapted and/or operative to releasably retain a nail holder 94. The nail holder 94 includes a tip 95 that is configured, adapted and/or operative to hold an intramedullary nail 96, while an end of the nail holder 94 distal the configured tip 95 (within the bore 26 in FIG. 8) is coupled to a positioner 28. As discussed below, the positioner 28 is configured, adapted and/or operative to rotate or position the intramedullary nail into certain angular or rotational orientations.

The tip 95 is configured to receive and/or retain the intramedullary nail 96 in a particular orientation. Particularly, the tip 95 is configured to retain the intramedullary nail 96 in a particular rotational or angular orientation with respect to a longitudinal axis of the intramedullary nail 96. As explained more fully below, this is to aid in the alignment of the intramedullary nail 96 with the bone fastener alignment and drill jig portion 32. In order to accomplish the above, the intramedullary nail 96 has an end 97 that is configured, adapted and/or operative to releasably mate with the configured tip 95 in the given orientation. As indicated above, the nail holder 94 is coupled to the positioner 28. The positioner 28 is configured, adapted and/or operative to orient or position the intramedullary nail in the particular rotational orientations as appropriate.

Figure 7:
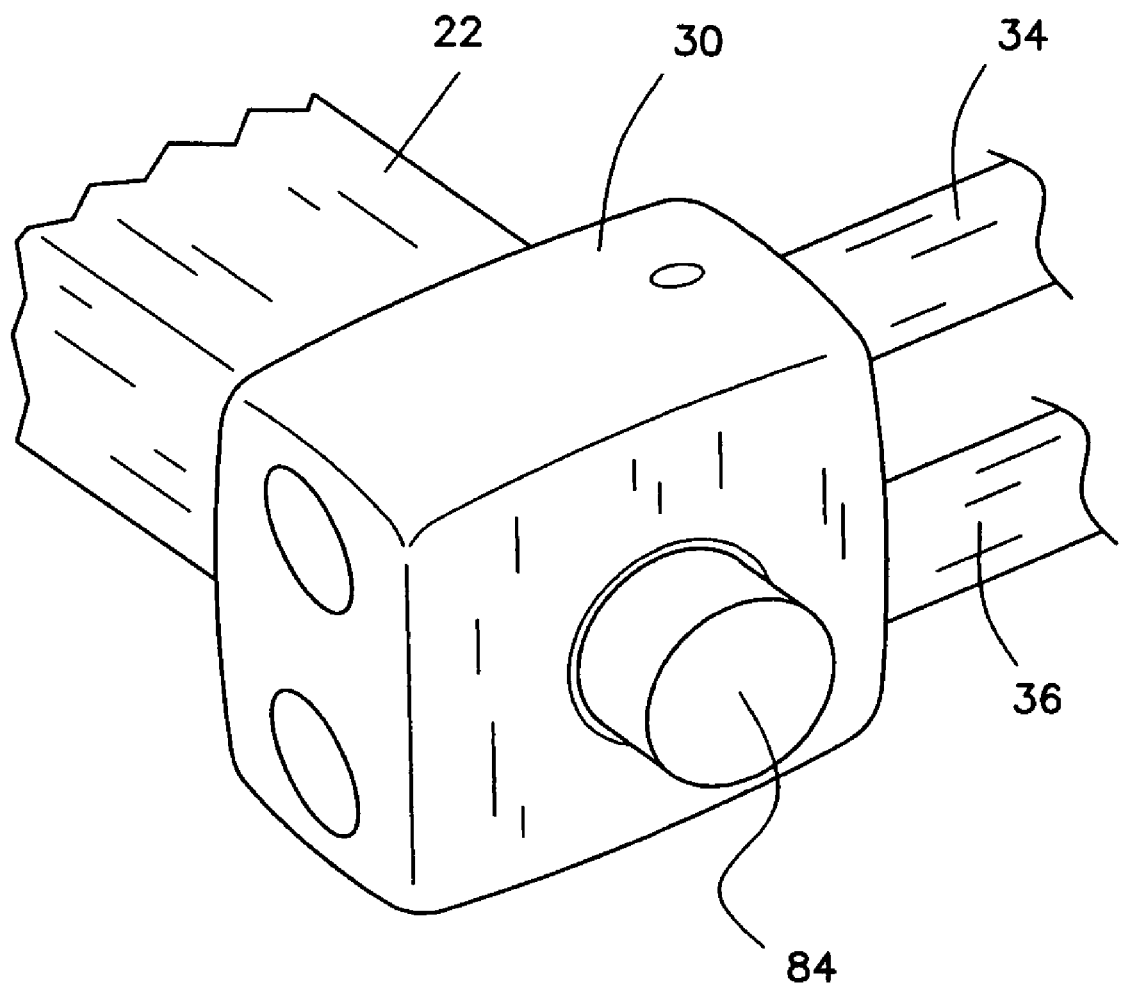
FIG. 7 is an enlarged perspective view of a portion of a pivot mechanism of the exemplary bone fastener targeting and compression/distraction guide for an intramedullary nail of FIG. 1.

The second end 30 is configured, adapted and/or operative to fixedly retain the bone fastener alignment and drill jig portion 32. When the intramedullary nail 96 is positioned in the bone, the nail arm 22 is pivotable about the intramedullary nail. This pivots the bone fastener alignment and drill jig portion 32 relative to the intramedullary nail 96. Particularly, and referring additionally to FIG. 7, the second end 30 includes a biased button 84 that is operatively coupled to a hinge 85 of the first end 24 through the nail arm 22 (as represented by the dashed line in FIG. 2). In a first or locked position, as shown in the figures, the nail arm 22 is in a non-pivoting or locked mode. In a second or unlocked position, the nail arm 22 is in a pivoting or unlocked mode. In the pivoting or unlocked mode, the arm 22, and thus the bone fastener alignment and drill jig portion 32 can be swung or pivoted about the hinge 85 and the bore/sleeve with bore 26. The button 84 is normally biased in the locked mode.

The bone fastener alignment and drill jig portion 32 is characterized by a first rail 34 and a second rail 36 each of which extends from the second end 30. The first and second rails 34 and 36 are parallel and form a support or track with a space therebetween. A first carriage or positioning block 38 is fixedly positioned on the first and second rails 34 and 36 a distance from the second end 30. The positioning block 38 includes a first bore 40, a second bore 42, and a third bore 44. The three bores 40, 42, and 44 extend from a top of a platform 46 formed as part of the positioning block 38 to a bottom of the positioning block 38 (i.e. therethrough). The bores 40, 42, and 44 are positioned so as to allow a drill bit, bone fastener, sleeve, or the like to extend through the space between the first and second rails 34 and 36.

The three bores 40, 42, and 44 correspond to three bores 98, 100, and 102 (see FIG. 7) in the intramedullary nail 96. Particularly, the positioning block 38 is fixedly situated on the first and second rails 34 and 36 a distance from the second block 30. This distance corresponds to the length of the nail holder 94 such that when an intramedullary nail is retained by the nail holder 94, the three bores 40, 42, and 44 to align with three bores 98, 100, and 102 in the intramedullary nail 96 (depending on the orientation of the nail, i.e. either the medial/lateral or the anterior/posterior orientations). For proper alignment, however, the positioner 28 must be set in one angular orientation. This particular angular orientation, in the particular embodiment, corresponds to the medial-lateral position.

The bone fastener alignment and drill jig portion 32 also includes a second carriage or positioning block 48 that is carried by the first and second rails 34 and 36. The second carriage 48 is movable along the first and second rails 34 and 36 as represented by the double-headed arrow adjacent the second carriage 48. The second carriage 48 includes a central platform 56 having two bores 52 and 54 that extend from a top of the platform 56 to a bottom of the second carriage 48 (i.e. therethrough). The bores allow a drill bit, bone fastener, sleeve, or the like to extend through the space between the first and second rails 34 and 36. The bore 52 is elongated or oval-shaped to allow static and dynamic placement (loading) of bone fasteners with respect to the intramedullary nail 96. As such, the bore 52 corresponds to either bore 104 or bore 114, each of which is elongated or oval-shaped, depending on the rotational orientation (i.e. medial/lateral or anterior/posterior) of the intramedullary nail 96.

Figure 5:
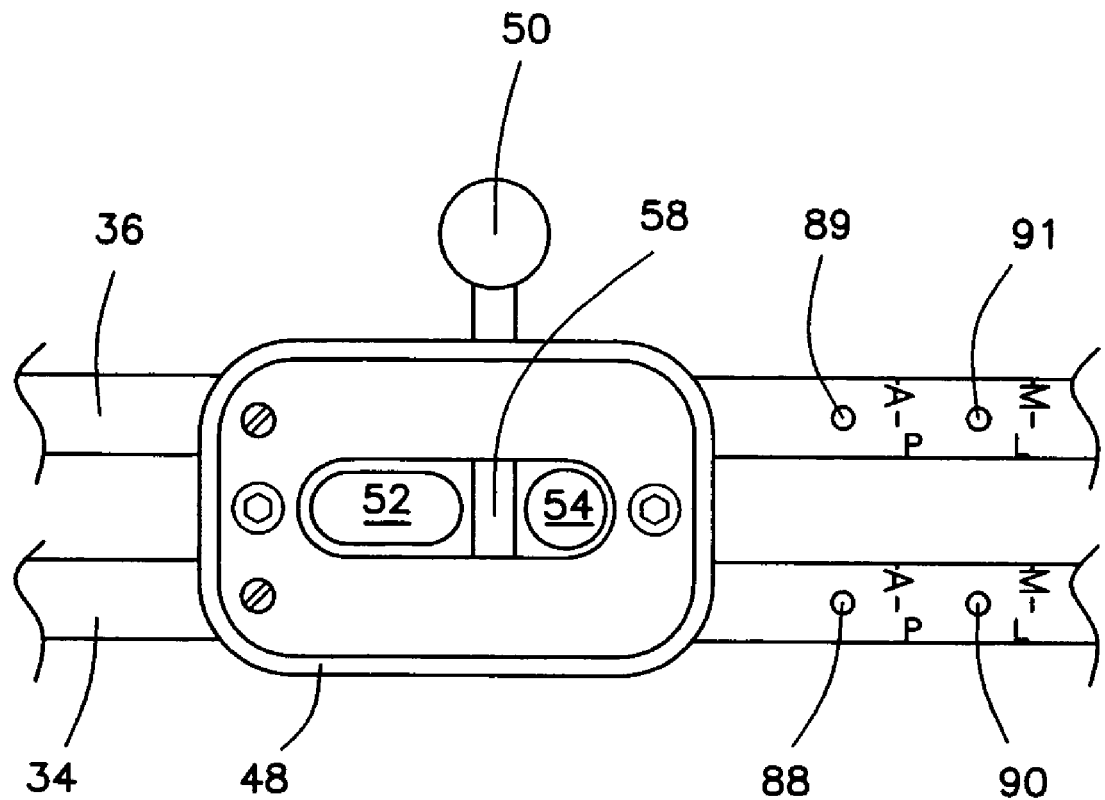
FIG. 5 is an enlarged plan view of an adjustable screw targeting carriage of the exemplary bone fastener targeting and compression/distraction guide for an intramedullary nail of FIG. 1.

The second carriage 48 is movable along the first and second rails 34 and 36 to accommodate various lengths of intramedullary nails, since the length of the intramedullary nail determines the axial position of the bores 104, 106, 114, and 116. A fixing/releasing mechanism controlled by a knob 50 is provided as part of the second carriage 48. Referring additionally to FIG. 5, the second carriage 48 is depicted in greater detail. The knob 50 is coupled to a shaft 58 that cooperates with a fixation mechanism within the second carriage body. The first and second rails each have holes or detents therein that correspond to lengths and rotational orientation (i.e. medial/lateral or anterior/posterior) of intramedullary nails. Depicted in FIG. 5 are anterior-posterior (A-P) detents, depressions or the like 88 and 89, and medial-lateral (M-L) detents 90 and 91, corresponding to a particular axial length of intramedullary nail. It should be appreciated that the first and second rails 34 and 36 have other sets of A-P and M-L detents corresponding to other axial lengths of intramedullary nails. Thus for each given length of intramedullary nail, the bone fastener alignment and drill jig portion 32 has two sets of carriage fixation detents (i.e. four detents); one set of carriage fixation detents (i.e. two detents) corresponding to an anterior-posterior (A-P) orientation, and one set of carriage fixation detents (i.e. two detents) corresponding to a medial-lateral (M-L) orientation. Each set of detents for a particular orientation comprises one detent per rail.

The knob 50 controls the free movement (release) and fixation (locking) of the carriage 48. When the knob 50 is in a position perpendicular to the rails 34 and 36 as depicted in FIG. 5, the corresponding shaft 58 and locking mechanism within the carriage 48 is in a release, unlocked, or free movement mode. The carriage 48 is thus free to move along the rails 34 and 36 in order to align the bores 52 and 54 with the appropriate bores (either the medial-lateral or anterior-posterior bores) in the intramedullary nail. When the knob 50 is in a position parallel to the rails 34 and 36, (not shown), the carriage 48 is locked. For proper orientation, the carriage 48 should be locked in the appropriate detents. Of course it should be appreciated that other locking/unlocking schemes may be employed.

With reference back to FIGS. 1–3, the bone fastener alignment and drill jig portion 32 further includes a compression/distraction adjustor or adjustment mechanism 76. The compression/distraction adjustor 76 is configured, adapted and/or operative to provide compression and/or distraction to the bone in conjunction with fixation rods, fasteners, screws and/or the like. Preferably, the compression/distraction adjustor 76 provides measured compression/distraction.

The compression/distraction adjustor 76 includes a third carriage or body 60 that is movably retained on the first and second rails 34 and 36. The body 60 includes a first bore 62 and a second bore 64 that extend from a top of a platform 66 to a bottom of the body 60 (i.e. therethrough). The bores 62 and 64 allow a drill bit, reamer, bone fastener, rod, sleeve, fixation device and/or the like to extend therethrough and through the space between the first and second rails 34 and 36. The compression/distraction adjustor 76 is movable along the first and second rails 34 and 36 within a predetermined axial length or path determined by an end cap 74 on one end and a length of an adjustment screw or the like 78.

Figure 6:
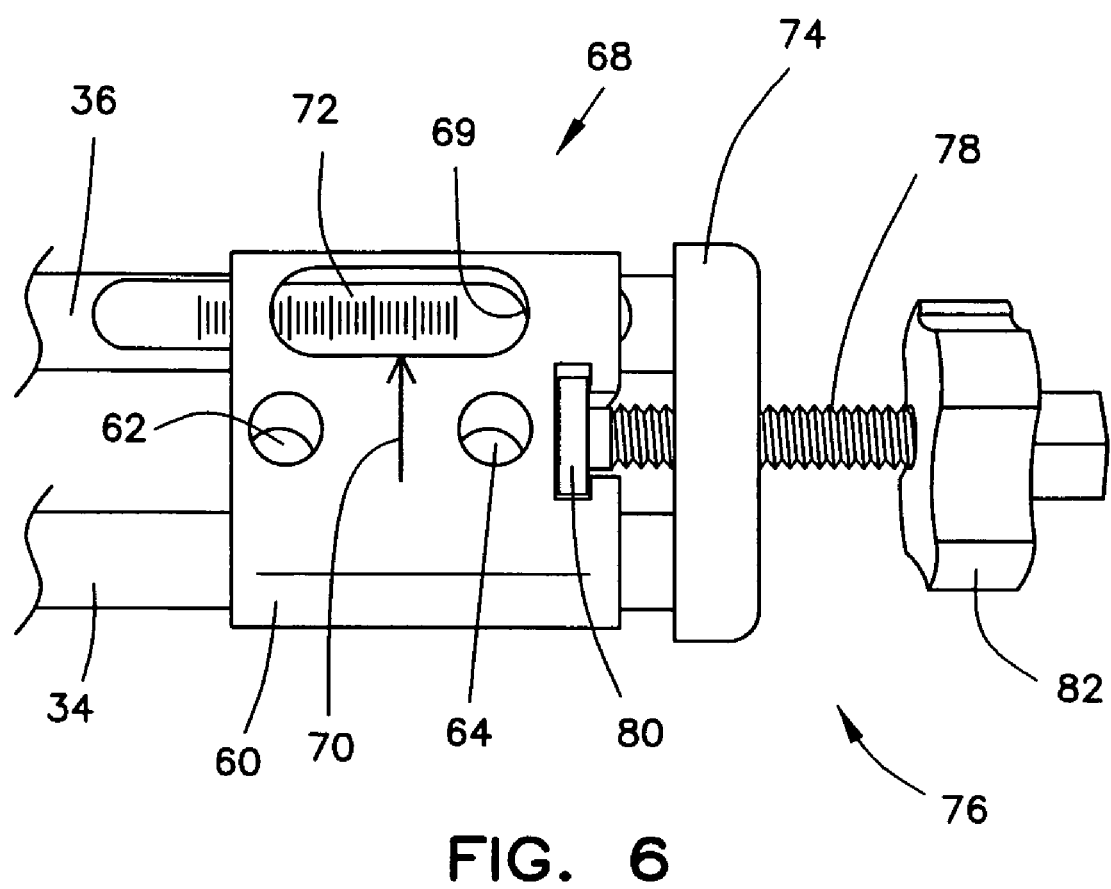
FIG. 6 is a top perspective view of an adjustable compression/distraction carriage/device of the exemplary bone fastener targeting and compression/distraction guide for an intramedullary nail of FIG. 1.

Referring additionally to FIG. 6, the compression/distraction adjustor 74 is depicted in greater detail. Particularly, the body 60 supports or retains a threaded cap 80 that threadedly receives an end of the adjustment screw 78. The adjustment screw 78 extends through a threaded bore in the end cap 74 and terminates in an adjustment knob 82. As the adjustment knob 82 is rotated, the adjustment screw 78 rotates to either advance the body 60 toward the nail arm 22 to provide compression, or retract the body 60 toward the end cap 74 to provide distraction. Particularly, fixation rods or the like (not shown) that extend through the bore 62, the bore 64, or both bores 62 and 64 and into the bone, transmit axial translation or movement of the body 60 along the rails 32 and 34 to axial movement of the bone. In this manner, movement of the body 60 in one direction (here axially to the left or toward the nail arm 22) provides compression of the bone, while movement of the body 60 in another direction (here axially to the right or toward the end cap 74) provides distraction of the bone.

The body 60 has an opening or window 69 adjacent the second rail 36. The second rail 36 has markings, indicia or indications 72 that provide a scale or the like that is visible through the window 69. A calibration marking or indicator 70 is provided on the body 60. The opening 69, indications 72, and indicator 70 provide a calibrator to visually show or indicate compression/distraction amount and/or force with respect to fixation devices extending through the bores 62 and 64 and into the bone. As the body 60 moves, the indicator 70 moves. In this manner, the indicator 70 points to the indications 70 to give a visual reading of the applied force of compression or distraction.

Figure 12:
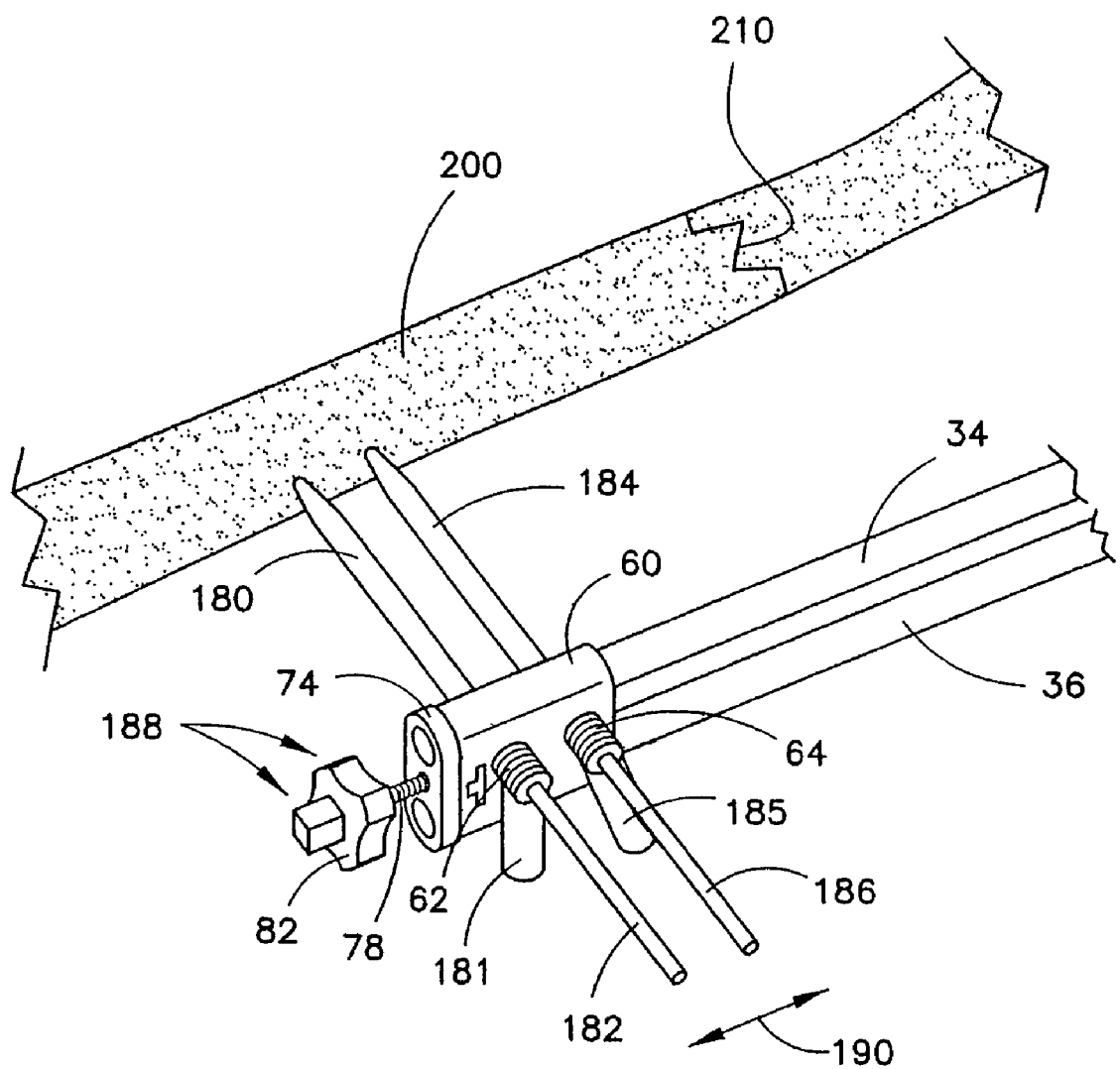
FIG. 12 is a perspective view of the compression/distraction carriage/device of the exemplary bone fastener targeting and compression/distraction guide for an intramedullary nail of FIG. 1 in use.

This is at least partially illustrated in FIG. 12 and reference is now made thereto. A bone 200 is depicted representing a bone in which an intramedullary nail has been inserted. The bone 200 has a fracture 210. After bone fasteners have been inserted through use of the fixed carriage 38 and before bone fasteners have been inserted through use of the movable carriage 48, compression or distraction of the bone 200 may be accomplished through use of the compression/distraction adjustor 60. A sheath 180 having a sheath handle 181 is shown extending through the bore 62 of the compression/distraction adjustor 60. A fixation rod 182 extends through the sheath 180 and contacts and/or penetrates the bone 200. In like manner, a sheath 184 having a sheath handle 185 is shown extending through the bore 64 of the compression/distraction adjustor 60. A fixation rod 186 extends through the sheath 184 and contacts and/or penetrates the bone 200. With the compression/distraction adjustor 60 fixed with respect to the bone, adjustment of the adjustment knob 82, as represented by the arrow 188, axially moves the body 60, as represented by the arrow 190. Depending on the direction of rotation of the adjustment knob 82, the body 60 axially travels to the left or right along the rail 34 and 36. As the body 60 moves so does the bone 200. Movement in the direction to the right in FIG. 12 provides compression of the bone 200, while movement in the direction to the left in FIG. 12 provides distraction. Once the desired amount of compression or distraction is set through knob 82 rotation and as indicated by the indicator 76, the distal bone fasteners may be set through the movable carriage 48.

Figure 13:
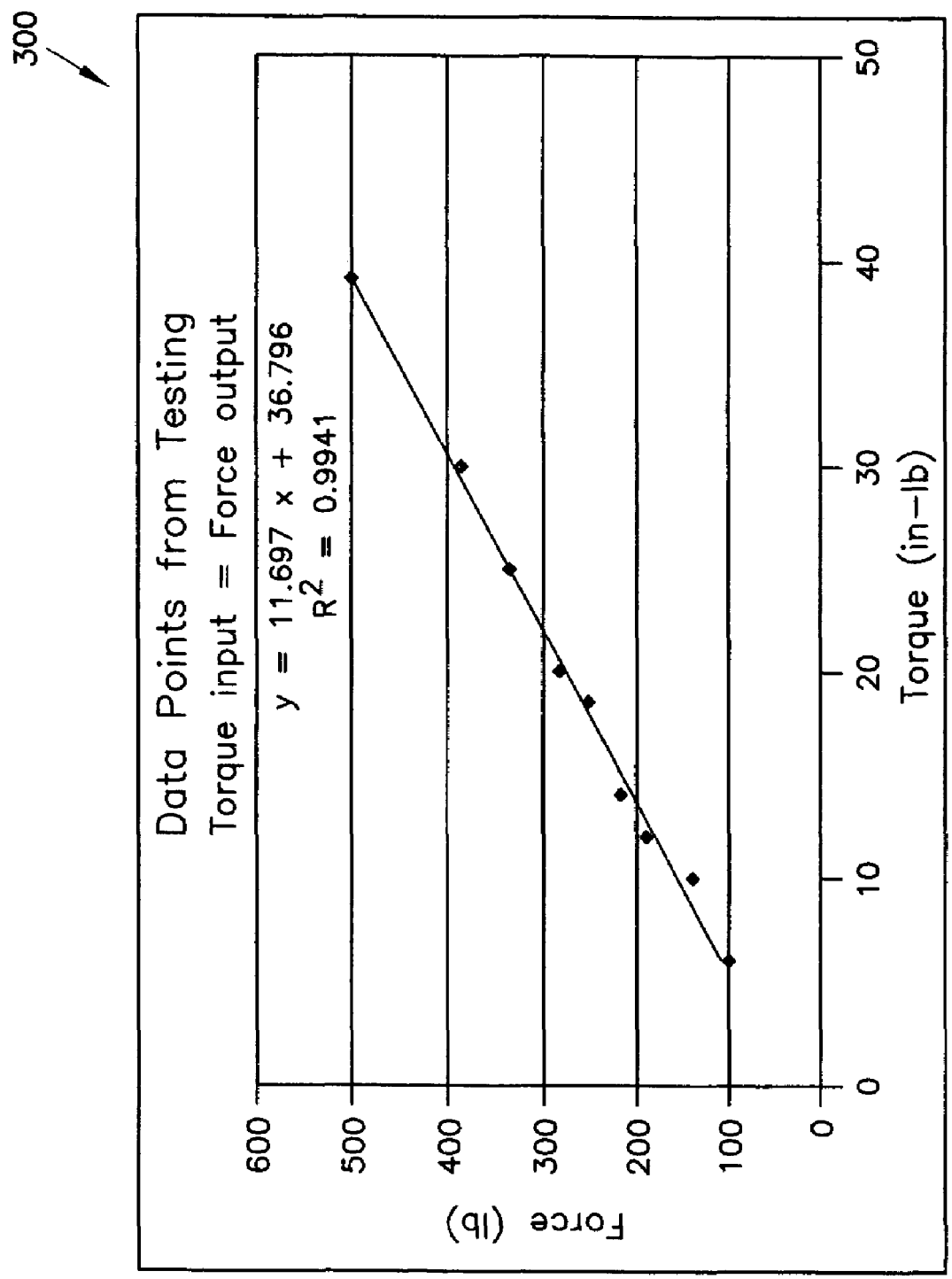
FIG. 13 is a graph of compression torque applied (torque input) by the compression/distraction carriage/device with resulting force (force output) applied across the bone.

Referring to FIG. 13, there is provided a graph, generally designated 300, that indicates input torque (in inch-pounds, in-lb) and the amount of force output (in pounds, lb) that is applied by the compression/distraction adjustor 60. The compression/distraction adjustor 60 provides measured and controlled force across the bone/fracture. Thus, during use, the surgeon may know the amount of force applied to the bone/fracture for a given amount of movement of the compression/distraction adjustor 60. For a given amount of movement, the controlled input provides a controlled or measured output.

The compression/distraction adjustor 60 may also provide alignment of the bone 200. Particularly, in addition to or solely, the compression/distraction adjustor 60 may function to provide alignment of the bone while the bone fasteners are appropriately positioned. Maintaining alignment of the bone 200 may be necessary or desired rather than providing compression or distraction.

It should be appreciated that the compression/distraction adjustment mechanism 76 may not necessarily be fixed with respect to the position shown in the figures. It is contemplated that the compression/distraction adjustment mechanism 76 may be positionable at any point along the rails 34 and 36. Thus, rather than just axial compression/distraction and/or alignment/fixation from an end of the bone, the compression/distraction adjustment mechanism 76 could provide compression/distraction and/or alignment/fixation from a point between the ends of the bone. One or more compression/distraction adjustment mechanisms may be provided, the one shown on the end and one "floating" mechanism. In another form, the end compression/distraction adjustment mechanism shown may be movable to any point along the rails 34 and 36. The compression/distraction adjustment mechanism 76 may be detachably attached to the rails 34 and 36.

Figure 4:
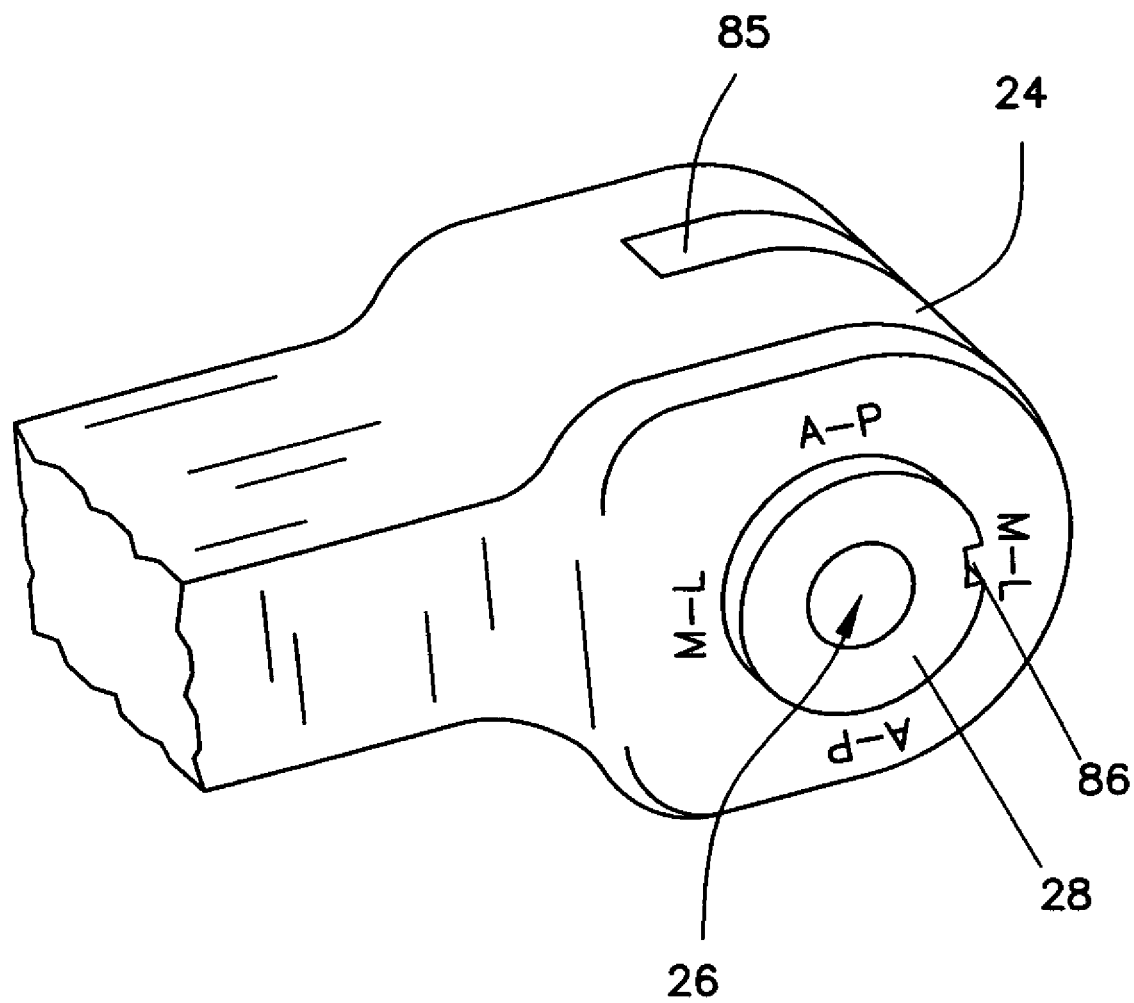
FIG. 4 is an enlarged perspective view of an intramedullary nail orientation device of the exemplary bone fastener targeting and compression/distraction guide for an intramedullary nail of FIG. 1.

Referring to FIG. 4, the positioner 28 of the first end or nail retention carrier 24 is shown. The positioner 28 has an indicator 86, here embodied as a notch, that indicates the rotational orientation of the intramedullary nail 96. The positioner 28 is rotatable into four (4) positions. Two of the four positions are labeled M-L (medial-lateral), while the other two positions are labeled A-P (anterior-posterior). The two M-L positions are 180° offset from one another. Likewise, the A-P positions are 180° offset from one another. Therefore, each position is 90° offset from another. In the case where in the intramedullary nail 96 is symmetrical about the longitudinal axis, the two like positions are identical. In the case where the intramedullary nail 96 is asymmetrical about a longitudinal axis (i.e. when the intramedullary nail 96 is curved), each position of the positioner 28 is different. When the positioner 28 is rotated, the nail holder 94 is rotated therewith. This, in turn, rotates the intramedullary nail 96. Particularly, when the positioner 28 is in the M-L position as depicted in FIG. 4, the bores 98, 100, and 102 of the intramedullary nail 96 (see FIG. 8 which shows the intramedullary nail 96 in a bone 200 having a fracture 210) are aligned with the appropriate bores 98, 100, and 102. Then, depending on whether the distal bone fasteners are to be implanted in the medial-lateral position or the anterior-posterior position, the positioner 28 either is kept in the same position or rotated.

Figure 9:
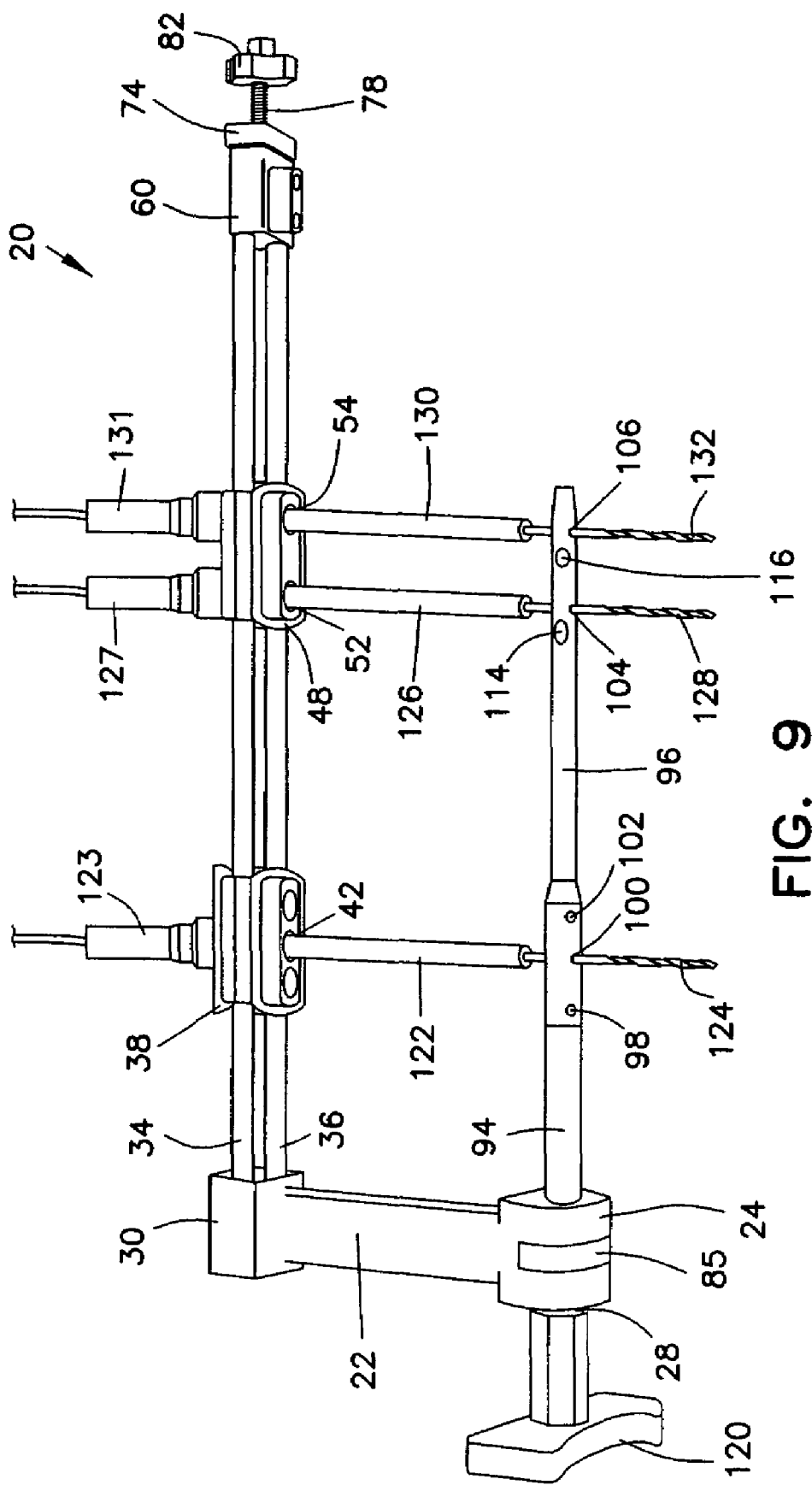
FIG. 9 is a perspective view of the exemplary bone fastener targeting and compression/distraction guide for an intramedullary nail of FIG. 1 shown retaining an intramedullary nail and fitted for alignment with bone drill bits.

Referring to FIG. 9, the intramedullary nail fastener targeting and bone compression/distraction device 20 is shown in an alignment position with respect to an intramedullary nail 96. It should be appreciated that the intramedullary nail 96 would normally be inserted within a bone, but for explanatory purposes, this is not the case. In FIG. 9, the intramedullary nail fastener targeting and bone compression/distraction device 20 is shown with a hammer pad 120 connected to the positioner 28. The hammer pad 120 is attached to the positioner before insertion of the intramedullary nail 96 into the medullary canal of the bone. The hammer pad 96 is utilized to advance the intramedullary nail 96 into the medullary canal in a manner known in the art.

The fixed carriage 38 is shown with a sheath 122 having a sheath handle 123 extending through the middle bore 42 of the carriage 38. A drill bit 124 or other drilling device or straight reamer extends through the sheath 122 and through the middle bore 100 of the intramedullary nail 96. Since the carriage 38 is fixed in its position on the rails 34 and 36, such alignment as shown is perfunctory.

The movable carriage 48 is shown aligned with the medial-lateral bores 104 and 106 of the intramedullary nail 96. The movable carriage 48 is positioned in the detents in the rails 34 and 36 according to the axial length and the rotational position of the intramedullary nail 96, here again, the medial-lateral position. Of course, it should be appreciated that the intramedullary nail fastener targeting and bone compression/distraction device 20 cannot be aligned in both the medial-lateral position and the anterior-posterior position at the same time. Thus, since the fixed carriage 38 is shown aligned in the medial-lateral position, so too is the movable carriage 48. A sheath 126 having a sheath handle 127 extends from the bore 52. A drill bit or other drilling device or straight reamer extends through the sheath 126 into the bore 104 of the intramedullary nail 96. A sheath 130 having a sheath handle 131 extends from the bore 54. A drill bit or other drilling device or straight reamer extends through the sheath 130 into the bore 54 of the intramedullary nail 96.

USE OF THE SUBJECT INVENTION

A use and/or application of the subject invention will now be described. It should be appreciated, however, that the below-described use/application of the subject invention is only exemplary of one manner of use. Other manners of use not specifically described herein are contemplated. As an example, the subject intramedullary nail screw targeting and bone compression/distraction guide may be used for tibiotalocalcaneal fusion. Regardless of the particular application, the following describes use of the subject intramedullary nail screw targeting and bone compression/distraction guide.

In preparation of use of the subject invention, the intramedullary canal of a bone is prepared for insertion of an intramedullary nail of an appropriate axial length. A guide wire may be implanted into the reamed intramedullary canal if appropriate. Once the site has been prepared for introduction of an intramedullary nail, the intramedullary nail is fixed onto the intramedullary nail screw targeting and bone compression/distraction guide 20 (see FIG. 8).

Next, as depicted in FIG. 4, the positioner 28 should be in the medial-lateral (M-L) position. This is true regardless of whether the medial-lateral (M-L) or anterior-posterior (A-P) distal screw placement option is chosen. If this is not observed, the distal intramedullary nail bores 98, 100, and 102 will be offset 90° from targeting attempts. With the hammer pad installed on the positioner 28 (see FIG. 9), the intramedullary nail 96 is driven or advanced into the prepared medullary canal. Once the intramedullary nail 96 is appropriately situated in the prepared medullary canal, holes are appropriately drilled through the bone utilizing the fixed carriage 38. In FIG. 9, a sheath 122 is shown installed in the fixed carriage 38 with a drill bit 124 extending therethrough ready to drill a hole in the bone that aligns with one of the holes (100) of the intramedullary nail 96. Once the bores for the holes 98, 100, and 102, bone fasteners or screws are installed. This may be accomplished by use of a T-handle screwdriver (not shown) to seat a bone screw.

If bone compression or distraction is desired, the compression/distraction mechanism (see, e.g. FIG. 12) is utilized in the manner set forth above. Once the appropriate compression or distraction is accomplished, the adjustable carriage 48 is set.

Particularly, the movable carriage 48 may then be positioned on the first and second rails 34 and 36 in the appropriate anterior-posterior or medial-lateral position (i.e. the movable carriage 48 detents) for the particular length of intramedullary nail and nail holes (either holes 104 and 106, or holes 114 and 116). The positioner 28 may also be rotated if necessary to appropriately position the intramedullary nail 96 in the anterior-posterior position. Once the movable carriage 48 is appropriately positioned, the knob 50 is set in the locked position to lock the carriage 48. Again, holes are appropriately prepared and bone screws are installed. It should be appreciated that at any time, the bone fastener alignment and drill jig portion 32 may be swiveled, pivoted, or swung about the intramedullary nail 96. Once all of the bone screws have been appropriately set, the intramedullary nail fastener targeting and bone compression/distraction device 20 may be removed.

Figure 10:
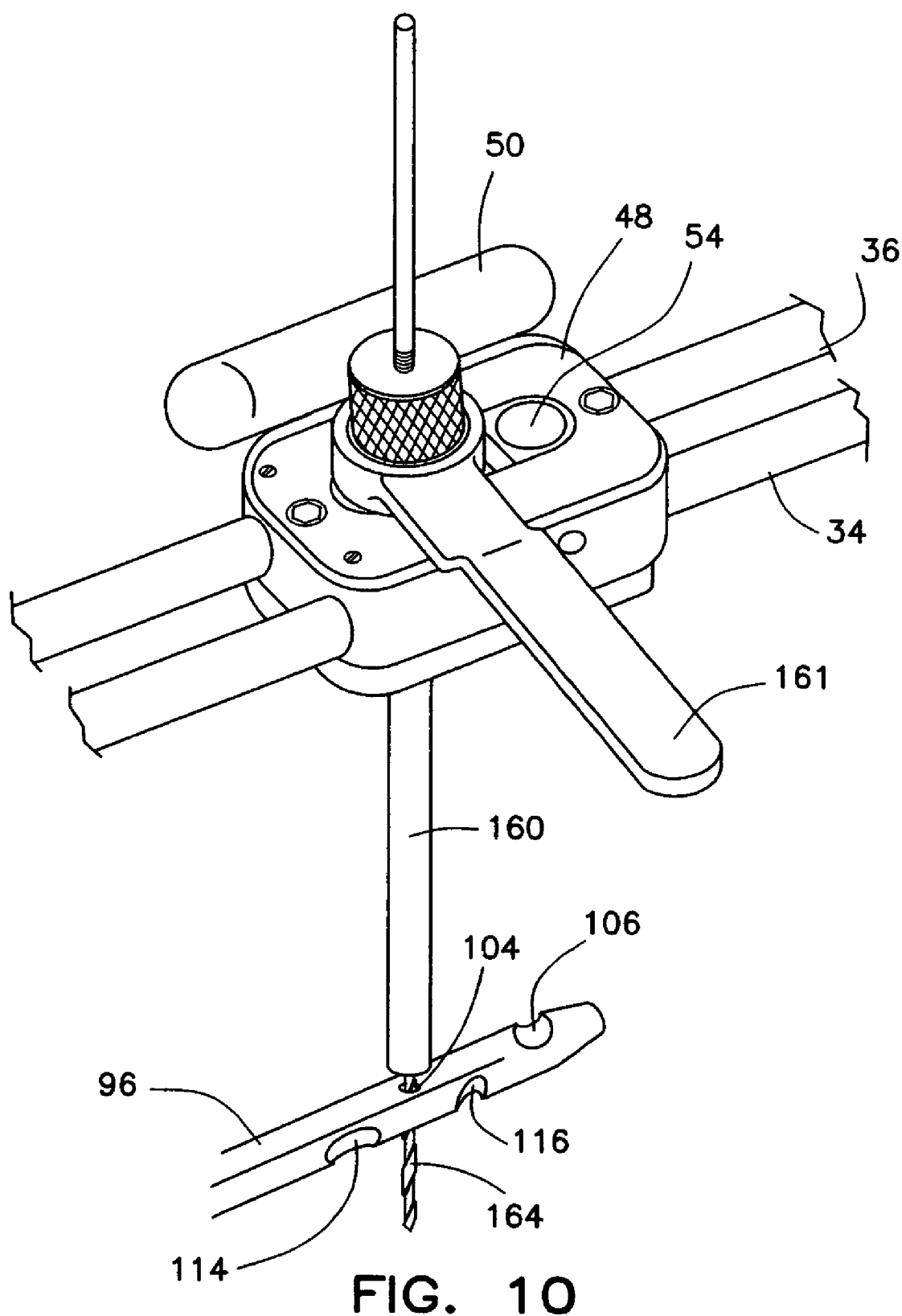
FIG. 10 is an enlarged perspective view of the movable carriage depicted in a static cross-locking position for drilling and fastener implantation with respect to the intramedullary nail.

Referring to FIG. 10 the movable carriage 48 is shown wherein static proximal cross-locking for a bone fastener with respect to the intramedullary nail 96 is shown being prepared. This is one of two options (the other of which is described below with respect to FIG. 11) when preparing and installing the bone fastener for the hole 104 or the hole 114. Initially, static cross-locking is accomplished when the sheath handle 161 is pointed away from the movable carriage locking knob 50. A sheath 160 extends through the bore 52 of the carriage 48. A drill bit 164 extends through the sheath 160 and is properly positioned to drill a hole for a bone screw such that the intramedullary nail 96 will not axially move. Since the hole 104 (as shown in FIG. 10, but should be understood that the same applies to hole 114) is elongated, there are choices for placement of the bone screw. When static cross-locking is desired, preparation of the bone as depicted in FIG. 10 and described above is used.

Figure 11:
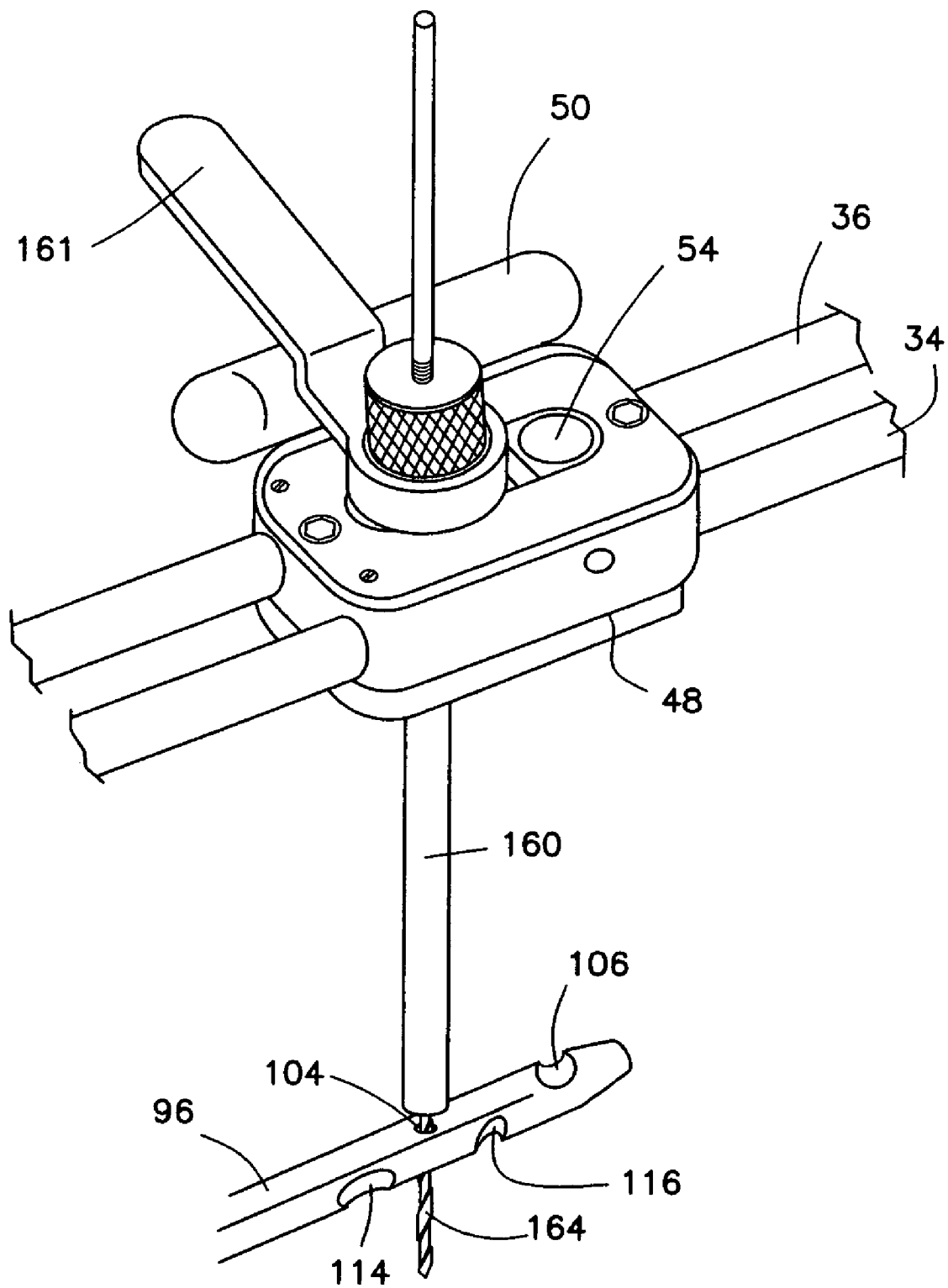
FIG. 11 is an enlarged perspective view of the movable carriage depicted in a dynamic cross-locking position for drilling and fastener implantation with respect to the intramedullary nail.

Referring to FIG. 11 the movable carriage 48 is shown wherein dynamic proximal cross-locking for a bone fastener with respect to the intramedullary nail 96 is shown being prepared. This is the second of two options (the other of which is described above with respect to FIG. 10) when preparing and installing the bone fastener for the hole 104 or the hole 114. Initially, dynamic cross-locking is accomplished when the sheath handle 161 is pointed toward the movable carriage locking knob 50. A sheath 160 extends through the bore 52 of the carriage 48. A drill bit 164 extends through the sheath 160 and is properly positioned to drill a hole for a bone screw such that the intramedullary nail 96 will axially move. Since the hole 104 (as shown in FIG. 10, but should be understood that the same applies to hole 114) is elongated, there are choices for placement of the bone screw. When dynamic cross-locking is desired, preparation of the bone as depicted in FIG. 11 and described above is used.

The subject invention provides various features and/or advantages. For example, the subject invention provides an external fixation device that is part of the targeting device to maintain alignment and to provide for compression and/or distraction. The subject invention is also easy to rotate around the intramedullary nail in order to move the device out of the viewing area (for radiographs and/or the like) and not lose position with respect to the intramedullary nail. Still further, the subject intramedullary nail screw targeting and bone compression/distraction guide provides a free sliding targeting device in order to align at multiple screw hole locations. Yet further, the subject intramedullary nail screw targeting and bone compression/distraction guide provides the ability to measure the amount of force across the fracture or fusion site.

There are a plurality of advantages of the subject invention arising from the various features of the intramedullary nail screw targeting and bone compression/distraction guide described herein. It will be noted that alternative embodiments of the intramedullary nail screw targeting and bone compression/distraction guide of the subject invention may not include all of the features described yet still benefit from at least some of the advantages of such features. Those of ordinary skill in the art may readily devise their own implementations of a intramedullary nail screw targeting and bone compression/distraction guide that incorporate one or more of the features of the subject invention and fall within the sprit and scope of the subject invention.

What is claimed is:

1. A targeting device for an intramedullary nail comprising:
    an intramedullary nail holder;
    an arm extending from said intramedullary nail holder;
    a support extending from said arm;
    a first bone fastener targeting block fixedly mounted on said support, the first bone fastener targeting block having at least one bore therethrough for alignment with a bore in an intramedullary nail held by the intramedullary nail holder;
    a second bone fastener targeting block movably mounted on said support; and
    a bone fixator mounted on said support and configured to provide compression to a bone, wherein said support comprises:
    a first rail; and
    a second rail spaced from and parallel to said first rail.

2. The targeting device of claim 1, wherein said bone fixator is operative to provide measured compression of the bone.

3. The targeting device of claim 1, wherein said bone fixator comprises a body adjustably mounted on said support.

4. The targeting device of claim 3, wherein said bone fixator further comprises an applied compression force indicator.

5. The targeting device of claim 1, wherein said first bone fastener targeting block is proximate said arm, said fixator is distal said arm, and said second bone fastener targeting block is between said first bone fastener targeting block and said fixator.

6. The targeting device of claim 1, wherein said bone fixator is configured to provide distraction to the bone.

7. The targeting device of claim 1, wherein said intramedullary nail holder is configured to provide a medial-lateral orientation of the intramedullary nail and an anterior-posterior orientation of the intramedullary nail.

8. The targeting device of claim 1, wherein said second bone fastener targeting block is configured to be releasably positioned in a medial-lateral position of targeting and an anterior-posterior position of targeting.

9. The targeting device of claim 8, wherein said second bone fastener targeting block is configured to be releasably positioned in a plurality of medial-lateral positions of targeting and a plurality of anterior-posterior positions of targeting.

10. The targeting device of claim 1, wherein said first bone fastener targeting block and said second bone fastener targeting block are configured to allow a bone fastener preparation and fixation device to extend between said first and second rails.

11. The targeting device of claim 1, wherein said arm is pivotable about said intramedullary nail holder.

12. An intramedullary nail bone fastener targeting apparatus comprising:
    an intramedullary nail holder;
    an arm extending from said intramedullary nail holder;
    a support extending from said arm;
    a fixed bone fastener targeting block positioned on said support, the fixed bone fastener targeting block configured to align with a first set of holes in any one of various lengths of intramedullary nails to guide an object from the fixed bone fastener targeting block to the first set of holes;
    a movable bone fastener targeting block positioned on said support to align with a second set of holes in any one of the various lengths of intramedullary nails; and
    a bone fixation mechanism positioned on said support and operative to provide compression or distraction to a bone in which the intramedullary nail is inserted, wherein said support comprises:
    a first rail; and
    a second rail spaced from and parallel to said first rail.

13. The intramedullary nail bone fastener targeting apparatus of claim 12, wherein said bone fixation mechanism is operative to indicate compression and distraction force applied to the bone.

14. The intramedullary nail bone fastener targeting apparatus of claim 12, wherein said bone fixation mechanism comprises:
    a body mounted on said support; and
    an adjustor coupled to said body and operative to move said body along said support.

15. The intramedullary nail bone fastener targeting apparatus of claim 12, wherein said fixed bone fastener targeting block is proximate said arm, said fixation mechanism is distal said arm, and said movable bone fastener targeting block is between said fixed bone fastener targeting block and said fixation mechanism.

16. The intramedullary nail bone fastener targeting apparatus of claim 12, wherein said intramedullary nail holder is configured to provide a medial-lateral orientation of the intramedullary nail and an anterior-posterior orientation of the intramedullary nail.

17. The intramedullary nail bone fastener targeting apparatus of claim 12, wherein said movable bone fastener targeting block is releasably positionable in a medial-lateral position of targeting and an anterior-posterior position of targeting.

18. The intramedullary nail bone fastener targeting apparatus of claim 17, wherein said movable bone fastener targeting block is releasably positionable in a plurality of medial-lateral positions of targeting and a plurality of anterior-posterior positions of targeting.

19. The intramedullary nail bone fastener targeting apparatus of claim 12, wherein said fixed bone fastener targeting block and said movable bone fastener targeting block are configured to allow bone fastener preparation and fixation device to extend between said first and second rails.

20. The intramedullary nail bone fastener targeting apparatus of claim 12, wherein said arm is pivotable about said intramedullary nail holder.

21. An intramedullary nail bone fastener targeting device comprising:
- an arm having a first end and a second end, said first end configured to receive an intramedullary nail holder that is configured to receive an intramedullary nail;
- a support extending from said second end;
- a first bone fastener targeting block fixedly retained on said support, said first bone fastener targeting block having a plurality of bores therethrough that are alignable with first bores in one end of an intramedullary nail that is adapted to be received by said intramedullary nail holder;
- a second bone fastener targeting block movably retained on said support, said second bone fastener targeting block having a plurality of bores therethrough that are alignable with second bores in another end of the intramedullary nail that are distal from the first bores regardless of length of the intramedullary nail; and
- a bone fixation block movably retained on said support, said bone fixation block having a bore therethrough that is adapted to retain a fixator that is attached to a bone, said bone fixation block providing compression or distraction of the bone via movement along said support while retaining the fixator.

22. The intramedullary nail bone fastener targeting device of claim 21, wherein said bone fixation block is operative to indicate compression and distraction force applied to the bone.

23. The intramedullary nail bone fastener targeting device of claim 21, wherein said bone fixation block comprises:
- a body mounted on said support; and
- an adjustor coupled to said body and operative to adjustably move said body along said support.

24. The intramedullary nail bone fastener targeting device of claim 21, wherein said first bone fastener targeting block is proximate said arm, said bone fixation block is distal said arm, and said second bone fastener targeting block is between said first bone fastener targeting block and said bone fixation block.

25. The intramedullary nail bone fastener targeting device of claim 21, wherein said first end is configured to rotate said intramedullary nail holder in a medial-lateral orientation and an anterior-posterior orientation.

26. The intramedullary nail bone fastener targeting device of claim 21, wherein said second bone fastener targeting block is releasably positionable in a medial-lateral position of targeting and an anterior-posterior position of targeting.

27. The intramedullary nail bone fastener targeting device of claim 26, wherein said second bone fastener targeting block is releasably positionable in a plurality of medial-lateral positions and a plurality of anterior-posterior positions.

28. The intramedullary nail bone fastener targeting device of claim 21, wherein said support comprises:
- a first rail; and
- a second rail spaced from and parallel to said first rail.

29. The intramedullary nail bone fastener targeting device of claim 28, wherein said bores of said first bone fastener targeting block and said bores of said second bone fastener targeting block are configured to allow bone fastener preparation and fixation device to extend between said first and second rails.

30. The intramedullary nail bone fastener targeting device of claim 21, wherein said arm is pivotable about said intramedullary nail holder.

31. A targeting device for an intramedullary nail comprising:
- a support;
- an intramedullary nail holder attached to the support and configured to retain an intramedullary nail having a first set of at least one bore and a second set of at least one bore;
- a first positioning block mounted on the support and having at least one bore configured such that when the intramedullary nail is retained by the intramedullary nail holder, the at least one bore of the first positioning block aligns with the at least one bore of the first set of at least one bore;
- a second positioning block mounted on the support and having at least one bore configured such that when the intramedullary nail is retained by the intramedullary nail holder, the at least one bore of the second positioning block aligns with the at least one bore of the second set of at least one bore; and
- an adjustor mounted on the support and movable with respect to the first positioning block, the adjustor having a bore therethrough configured to retain a bone contacting and/or penetrating device when the intermedullary nail is inserted into the medullary canal of a bone.

32. The targeting device of claim 31, wherein the second positioning block is releasably positionable on the support in a plurality of medial-lateral positions and a plurality of anterior-posterior positions.

33. The targeting device of claim 31, further comprising:
- an adjustment knob operably engaging the adjustor such that as the adjustment knob is rotated, the adjustor moves along the support arm.

34. The targeting device of claim 33, wherein the adjustor and the first positioning block define a first axis, the targeting device further comprising:
- an applied force indicator operably connected to the adjustor to indicate the force applied to a bone through the bone contacting and/or penetrating device along an axis parallel to the first axis.

* * * * *